(12) United States Patent
Ferguson

(10) Patent No.: US 7,794,452 B2
(45) Date of Patent: Sep. 14, 2010

(54) DEVICE AND METHOD FOR POSITIONING AND ATTACHING A MEMBER SUCH AS AN IMPLANT OR JIG

(75) Inventor: Joe William Ferguson, Collierville, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1731 days.

(21) Appl. No.: 10/967,836

(22) Filed: Oct. 18, 2004

(65) Prior Publication Data
US 2006/0084944 A1 Apr. 20, 2006

(51) Int. Cl.
*A61B 17/00* (2006.01)
*A61B 17/56* (2006.01)

(52) U.S. Cl. .................. 606/1; 606/87; 606/104

(58) Field of Classification Search .......... 606/1, 606/86, 87–89, 53–60, 104, 246–253, 258–265; 604/93.01, 264
See application file for complete search history.

(56) References Cited

U.S. PATENT DOCUMENTS

| | | | |
|---|---|---|---|
| 2,248,054 A | 7/1941 | Becker | |
| 3,892,232 A * | 7/1975 | Neufeld | 606/80 |
| 4,681,103 A * | 7/1987 | Boner et al. | 606/1 |
| 5,152,765 A | 10/1992 | Ross et al. | |
| 5,203,784 A | 4/1993 | Ross et al. | |
| 5,217,486 A | 6/1993 | Rice et al. | |
| 5,224,946 A | 7/1993 | Hayhurst et al. | |
| 5,246,441 A | 9/1993 | Ross et al. | |
| 5,351,692 A * | 10/1994 | Dow et al. | 600/463 |
| 5,354,292 A | 10/1994 | Braeuer et al. | |
| 5,370,646 A | 12/1994 | Reese et al. | |
| 5,423,860 A | 6/1995 | Lizardi et al. | |
| 5,466,243 A | 11/1995 | Schmieding et al. | |
| 5,584,860 A | 12/1996 | Goble et al. | |
| 5,649,931 A | 7/1997 | Bryant et al. | |
| 5,658,289 A | 8/1997 | Boucher et al. | |
| 5,662,658 A | 9/1997 | Wenstrom, Jr. | |
| 5,690,677 A | 11/1997 | Schmieding et al. | |
| 5,730,744 A | 3/1998 | Justin et al. | |
| 5,904,685 A | 5/1999 | Walawalkar | |
| 5,951,559 A | 9/1999 | Burkhart | |
| 5,993,451 A | 11/1999 | Burkhart | |
| 5,993,459 A | 11/1999 | Larsen et al. | |
| 6,041,485 A | 3/2000 | Pedlick et al. | |
| 6,371,968 B1 * | 4/2002 | Kogasaka et al. | 606/190 |
| 6,436,100 B1 | 8/2002 | Berger | |
| 6,575,974 B2 | 6/2003 | Gotfried | |
| 6,626,913 B1 | 9/2003 | McKinnon et al. | |

(Continued)

*Primary Examiner*—Ahmed M Farah

(57) ABSTRACT

A surgical device for positioning a member and attaching the member within the patient. A first element comprises a shaft having a driver at distal end. A second element includes an internal bore extending through the length, and a coupler at a second end to attach to the member. The shaft is sized to fit within the bore with the driver end positioned adjacent to the member to affix a fastener. In use, the second element is attached to the member. The first element is inserted into the second element and may be used as a striking instrument to affix the member within the patient. The second element is then used as a guide for positioning a fastener relative to the member, and the driver of the first element is used to mount the fastener to the bone and attach the member.

11 Claims, 7 Drawing Sheets

U.S. PATENT DOCUMENTS

| | | |
|---|---|---|
| 6,652,533 B2 | 11/2003 | O'Neil |
| 6,675,974 B2 | 1/2004 | Ballin et al. |
| 6,723,100 B2 | 4/2004 | Biedermann et al. |
| 2003/0023243 A1* | 1/2003 | Biedermann et al. .......... 606/73 |
| 2006/0041317 A1* | 2/2006 | Hazebrouck et al. ...... 623/23.39 |

* cited by examiner

DEVICE AND METHOD FOR POSITIONING AND ATTACHING A MEMBER SUCH AS AN IMPLANT OR JIG

BACKGROUND

During a surgical procedure, it is often necessary to attach a member, such as a jig or implant, within a patient. The member is initially accurately positioned relative to the bone, and then permanently attached thereto. Various devices are available for inserting and accurately positioning the member into a patient's body. Further, there are separate devices for permanently attaching the member.

The surgeon performing the procedure may have a difficult time manipulating multiple instruments. Multiple instruments require the surgeon to simultaneously make fine and precise movements with each hand to position and attach the member. Additionally, the surgeon may also need to perform other steps requiring them to free at least one of their hands. This requires the surgeon either to hold multiple tools with one hand, or remove one or both tools from the patient. To make the procedure more difficult, many surgical procedures are performed in a minimally intrusive manner. The access to the bone, and thus the space to manipulate the instruments, is at a minimum. Further, the surgeon's view of the bone and member may be blocked by the multiple devices and his hands and arms.

Fasteners, such as screws and the like, are often used to permanently attach the member to the bone. The fasteners are placed into the surgical area relative to the member, and then driven into the bone to permanently attach the member. The fasteners are often small in size making them difficult to manipulate and position. It is also important that the fasteners not be dropped or lost, either into the surgical area where they must be accessed and removed, or dropped from the sterile area where they must be either discarded or re-sterilized.

SUMMARY

An embodiment of the present invention is directed to a device and method for positioning and attaching a member within a patient. The device includes one element that attaches to the member for positioning within the patient. The element acts as a guide and sheath to receive a second element to insert a fastener into the patient to permanently attach the member.

DETAILED DESCRIPTION

Figure 1:
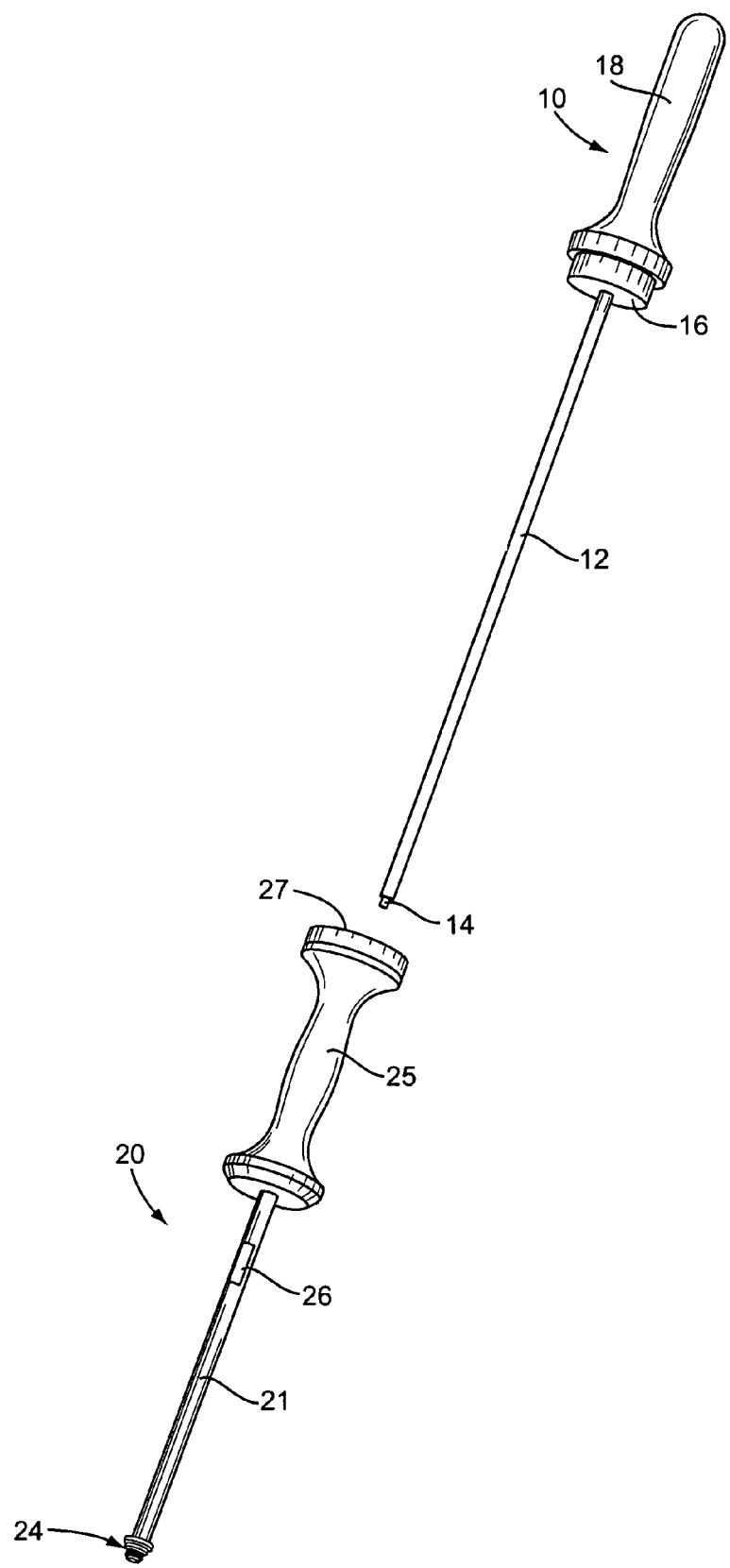
FIG. 1 is a perspective view of the first element separated from a second element according to one embodiment of the present invention.
Figure 2:
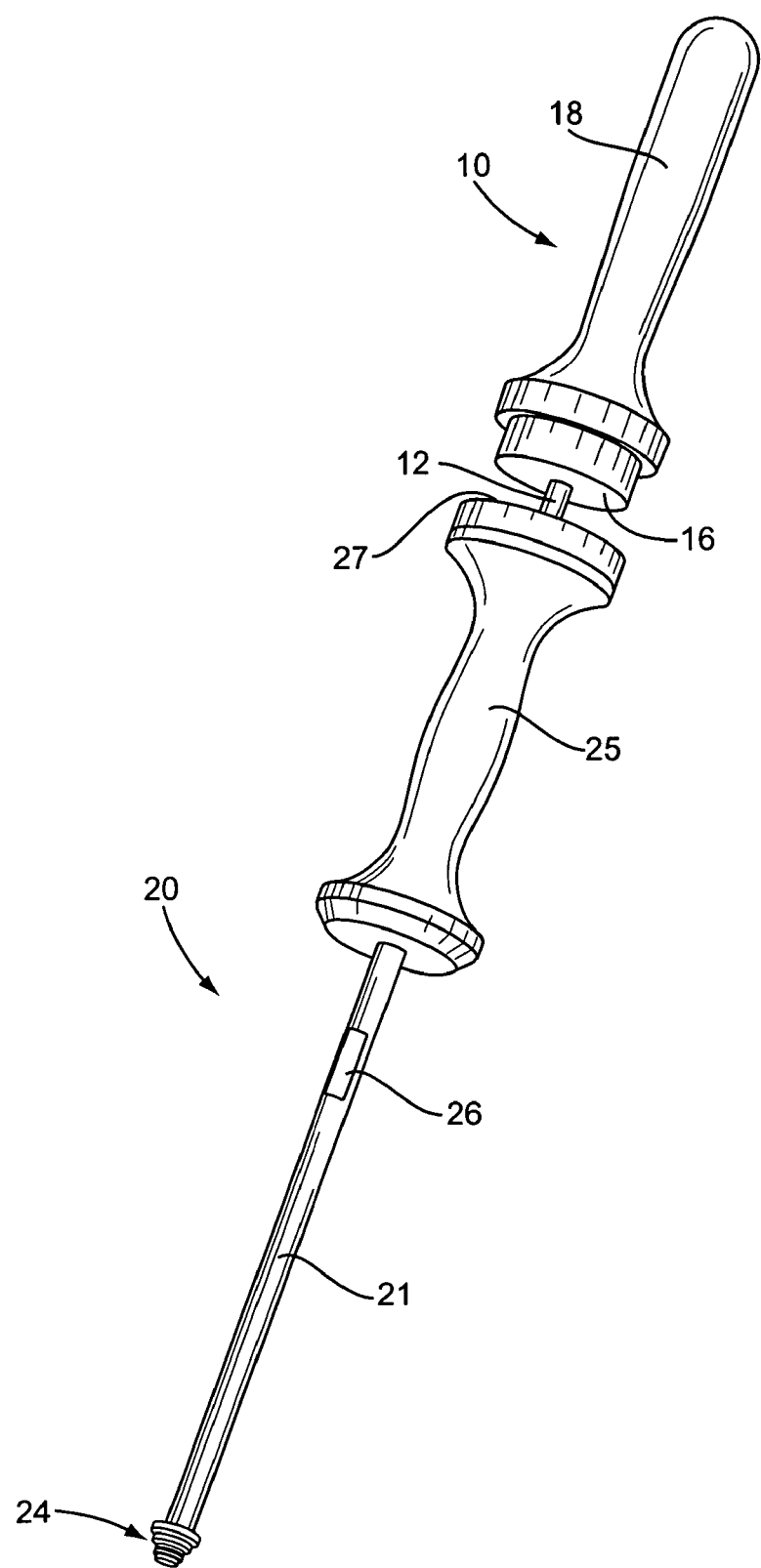
FIG. 2 is a perspective view of the first element positioned within the second element according to one embodiment of the present invention.

An embodiment of the present invention is directed to a surgical device for positioning and attaching a member within the patient. FIG. 1 illustrates one embodiment having a first element 10 and a second element 20. The first element 10 comprises a shaft 12 having a driver 14 at distal end. The second element 20 includes an internal bore 22 (FIG. 6) extending through the length, and a coupler 24 at a second end to attach to the member 80. The second element 20 is attached to the member 80 and the shaft 12 is sized to fit within the bore 22 with the driver 14 positioned adjacent to the member 80. The driver 14 is then used to mount with the fastener 90 and permanently attach the member 80.

The first element 10 provides a means for inserting the attaching fastener 90 to the patient, and may also provide a striking force to the second element 20. The driver 14 is positioned at a distal end of the first element 10. The driver 14 mates with a head of the fastener 90 to rotate the fastener 90 and insert it into the patient. The driver 14 may have a variety of shapes, including hex, Phillips, regular single-slot, square, Torx, etc.

The shaft 12 is sized to fit within and rotate within the bore 22. The shaft 12 and bore 22 may have the same cross-sectional shape, or may have different shapes. In one embodiment, both have a substantially circular cross-sectional shape. The shaft 12 may be constructed of a solid material, or may be hollow depending upon the required strength parameters.

A striking surface 16 is positioned towards the proximal end of the shaft 12 to provide a striking force to the second element 20. In one embodiment, the striking surface 16 has a larger width than the shaft 12, and is substantially perpendicular to the shaft 12. Other embodiments may include various sizes of the striking surface 16, and the striking surface 16 may be orientated at a variety of angles relative to the shaft 12. In the embodiment illustrated in FIG. 1, the shaft 12 is positioned at a central section of the striking surface 16. A handle 18 is positioned adjacent to the striking surface 16. The handle 18 provides an area for the surgeon to grip and manipulate the first element 10. The striking surface 16 may be a part of the handle 18, or they may be separate components each mounted on the shaft 12.

Figure 3:
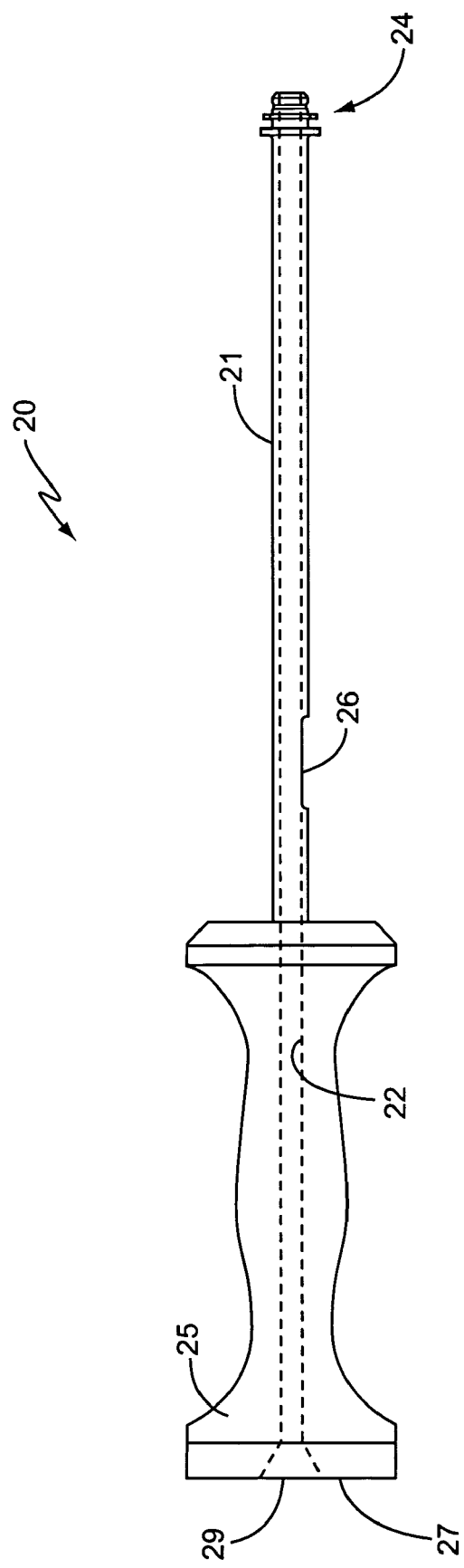
FIG. 3 is a side view of the second element according to one embodiment of the present invention.

The second element 20 provides for attachment to the member 80, and acts as a sheath and guide for the first element 10 and for the fastener 90. The second element 20 includes a first end having a contact surface 27, a second end having a coupler 24, and a bore 22 extending there between. FIG. 3 illustrates a side view of the bore 22 extending the length of the second element 20 from a handle 25 to the coupler 24. The bore 22 has a width to accommodate the shaft 12 with driver 14, and allow rotation of the first element 10 relative to the second element 20 necessary to secure the fastener 90 within the patient. The width of the bore 22 may be substantially equal along the length of the second element 20, or may vary. A flared section 29 having a greater width than a remaining section of the bore 22 may be positioned at the first end to guide the insertion of the first element 10 and/or fastener 90.

A window 26 is positioned within the second element 20 to access the bore 22. The window 26 provides a means for the surgeon to insert a fastener into the bore 22 such that it will be guided down towards the member 80. The window 26 is distanced from the distal end of the second element 20 such that the surgeon can remotely insert the fastener 90 into the member 80. Locating remotely is helpful when access to the member 80 is limited and may not be possible were the surgeon is required to actually manipulate their fingers to directly access the member 80. In the event a fastener 90 is accidentally dropped during insertion, the remote location of the window 26 may cause the fastener 90 to drop harmlessly away from the surgical area instead of potentially into the patient. The window 26 is sized to accommodate the various sizes of fasteners 90. In the embodiment of FIG. 3, the window 26 has a greater length than width, although various shapes and sizes are possible. The embodiment of FIG. 3 illustrates the window 26 positioned within the neck 21, however, the window 26 may also be positioned within the handle 25. In one embodiment, the window 26 is positioned closer to the contact surface 27 than to the coupler 24.

Handle 18 is positioned on the proximal end for the surgeon to grasp and manipulate the second element 20. A contact surface 27 on the proximal end provides a surface for striking the second element and temporarily mounting the member 80. In one embodiment, the contact surface 27 has a width greater than the bore 22, and is substantially perpendicular to the bore 22. Other embodiments may include the contact surface 27 having a variety of widths, and positioned at a variety of angles relative to the bore 22. The contact surface 27 may be substantially parallel with the striking surface 16 when the shaft 12 is inserted within the bore 22.

Figure 4:
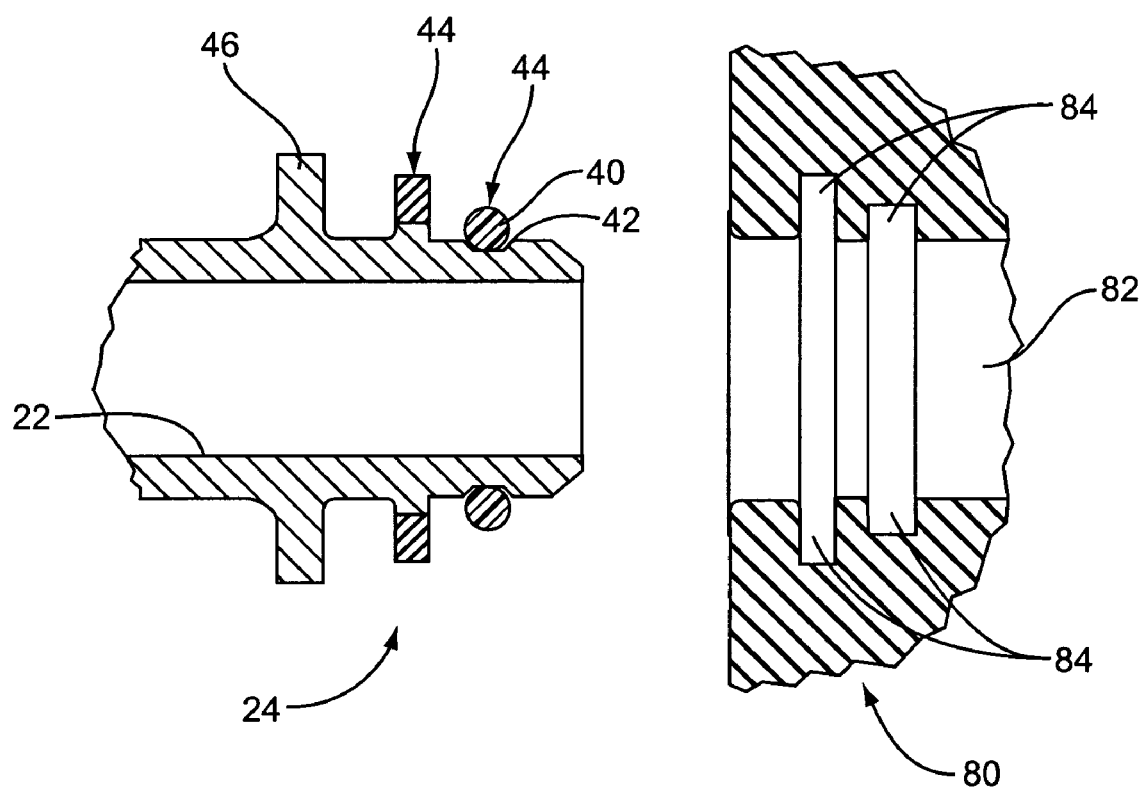
FIG. 4 is a partial cross-sectional view of the coupler and aperture of the member according to one embodiment of the present invention.

The coupler 24 is positioned at the distal end to temporarily connect the member 80 and second element 20 during insertion or removal. A variety of coupler embodiments are contemplated in the present invention. FIG. 4 illustrates one embodiment of the coupler 24 having a width that generally conforms to the width of an aperture 82 in the member 80. Coupler 24 includes one or more extensions 44 having a greater width than the aperture 82. The extensions 44 are constructed to compress as the coupler 44 enters into the aperture 82 and then expand to a larger width into grooves or slots 84 within the member 80.

The extensions 44 may comprise a variety of embodiments, including a flexible O-ring, a C-clip, an expandable collet, or an extension spring with the ends fastened together to form a ring (i.e., garter spring). In another embodiment, extension 44 is a mechanical elliptical spring available from Bal Seal Engineering Co, Inc. of Foothill Ranch, Calif.

In each of these embodiments, the extension 44 is biased outward at an extended position prior to insertion into the member 80. As the coupler 24 is inserted into the member 80, the insertion force overcomes the bias of the extension 44 forcing it towards a retracted position that can fit within the aperture 82. As the member 80 is inserted to the proper depth, the extension 44 expands outward towards their original size and into the slot 84. Coupler 44 may further include a flange 46 having a width larger than the aperture 82. The flange 46 contacts the surface of the member when the coupler 24 is fully seated.

The coupler 24 may include more than one extension 44. In multiple-extension embodiments, the extensions 44 may be the same or different types and sizes. In the embodiment of FIG. 4, the coupler 24 includes two separate extensions 44. The distal extension 44 comprises an O-ring 40 seated within an indent 42, and the second larger extension 44 comprises a C-clip.

In another embodiment, one or more of the extensions 44 are mounted within the grooves 84 and have an inner diameter that extends into the aperture 82. The extensions 44 compress as the chamfer on the distal end of the coupler 24 begins to pass through the inner diameter. In one embodiment, the extensions seat within the groove 42 when the coupler 24 is seated within the member 80.

Figure 5:
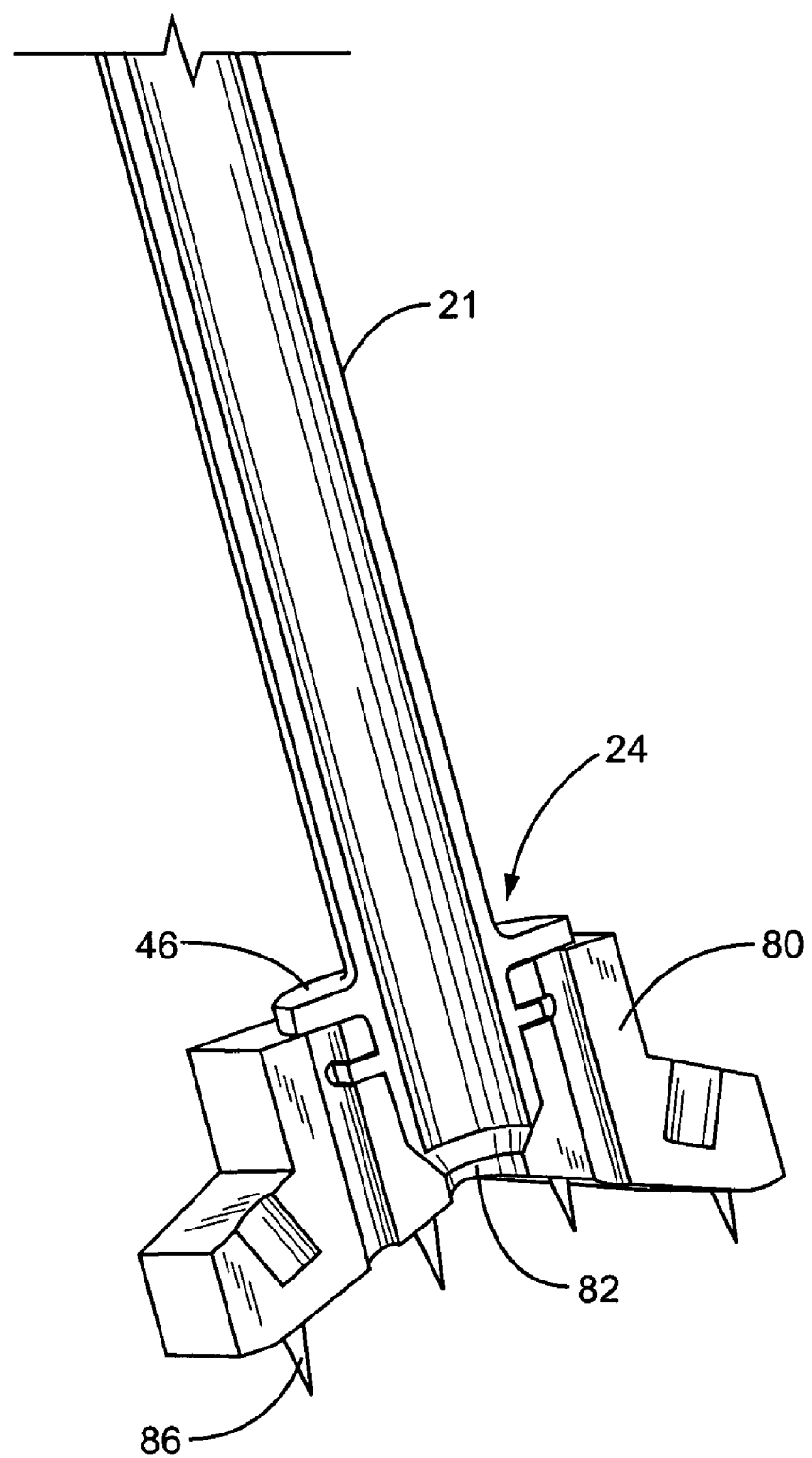
FIG. 5 is a partial cross-sectional view of the second element attached to a member according to one embodiment of the present invention.

FIG. 5 illustrates the coupler 24 mounted within an aperture 82 of the member 80. This embodiment features a single extension 44 extending into a corresponding slot 84 in the member. The flange 46 is in contact with the upper surface of the member 80 to control the amount of insertion of the coupler 24 into the aperture 82. In this configuration, the second element 20 can be manipulated to accurately position the member 80 relative to the patient. Once positioned, a striking force applied to the second element 20 is transferred to the member 80 to drive the teeth 86 into the bone. The teeth 86 are adequate to temporarily maintain the position of the member 80 thus allowing the surgeon to let go off the second element 20.

Figure 6:
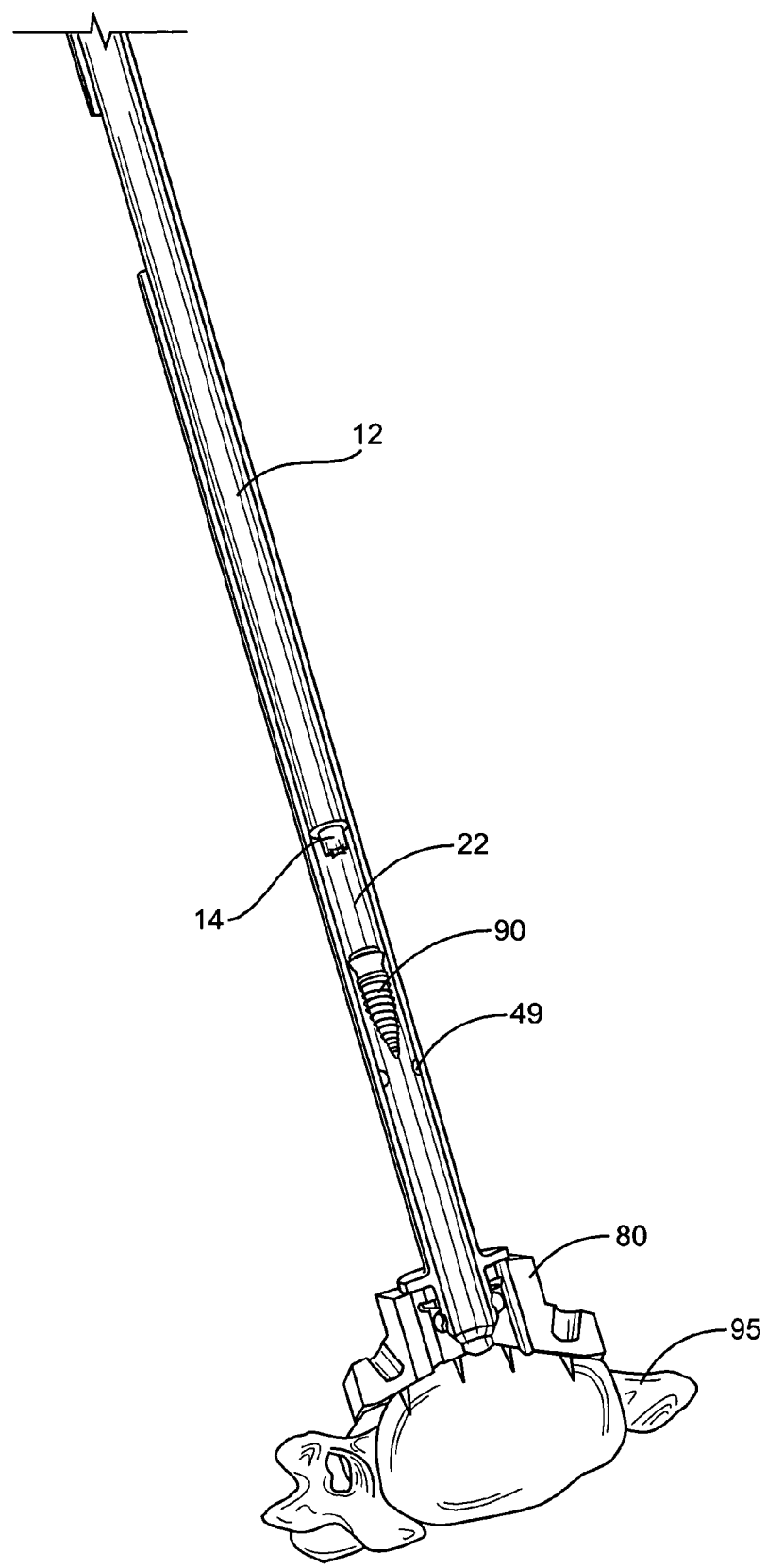
FIG. 6 is a partial cross-sectional view of the first element positioned within the second element according to one embodiment of the present invention.

FIG. 6 illustrates the fastener 90 inserted into the bore 22. The shaft 12 of the first element 10 is inserted into the bore 22 and the driver 14 engages the head of the fastener 90 to attach the fastener and member 80 to the bone 95. The bore 22 has an adequate width relative to the shaft 12 to allow the shaft 12 to rotate to secure the fastener 90 to the bone. The term "bone" is used in a general sense to refer to the structure in the body that maintains the member 80. This may include both hard or soft anatomy.

A catch 49 may be positioned in the bore 22 to prevent the fastener 90 from moving entirely out of the coupler 24 when it is initially inserted into the bore 22. The catch 49 has a smaller width then the remainder of the bore 22 and is smaller than the fastener 90. The catch 49 is flexible such that the first element 10 can apply a force to move the fastener beyond the catch.

In use, the member 80 is initially mounted via the coupler 24 to the second element 20. The member 80 is then positioned at the mounting position relative to the bone 95. A striking force is than applied to the contact surface 27 by the first element 10. The shaft 12 is inserted into the bore 22 and the striking surface of the first element is brought into contact with the contact surface 27 one or more times to drive the member teeth 86 into the bone 95. The teeth 86 in the bone 95 are adequate to temporarily maintain the position such that the surgeon can let go of the second element 20.

A fastener 90 is then inserted into the bore 22 either through the window 26 or through the flared end 29. The fastener 90 moves through the bore either via gravity or through assistance with the shaft 12 and driver 14. The coupler 24 is inserted over the aperture 82 within the member 80 and the fastener is delivered via the bore 22 to the attachment position. The driver 14 mates with a driving feature on the head of the fastener and the first element 10 is rotated to drive the fastener 90 into the bone 95. During this step, the surgeon may hold the second element 20. Once the fastener 90 is securely mounted, the coupler 24 is removed from the member 80.

In one embodiment, the length of the shaft 12 of the first element 10 that extends from the striking surface 16 to the end of the driver 14 is greater than the length of the second element 20. This length is necessary for the first element 10 to fully insert the fastener 90 to the member 80. In one specific embodiment, the length of the shaft 12 is about 10 inches and the length of the second element 20 is about 9.9 inches.

Figure 7:
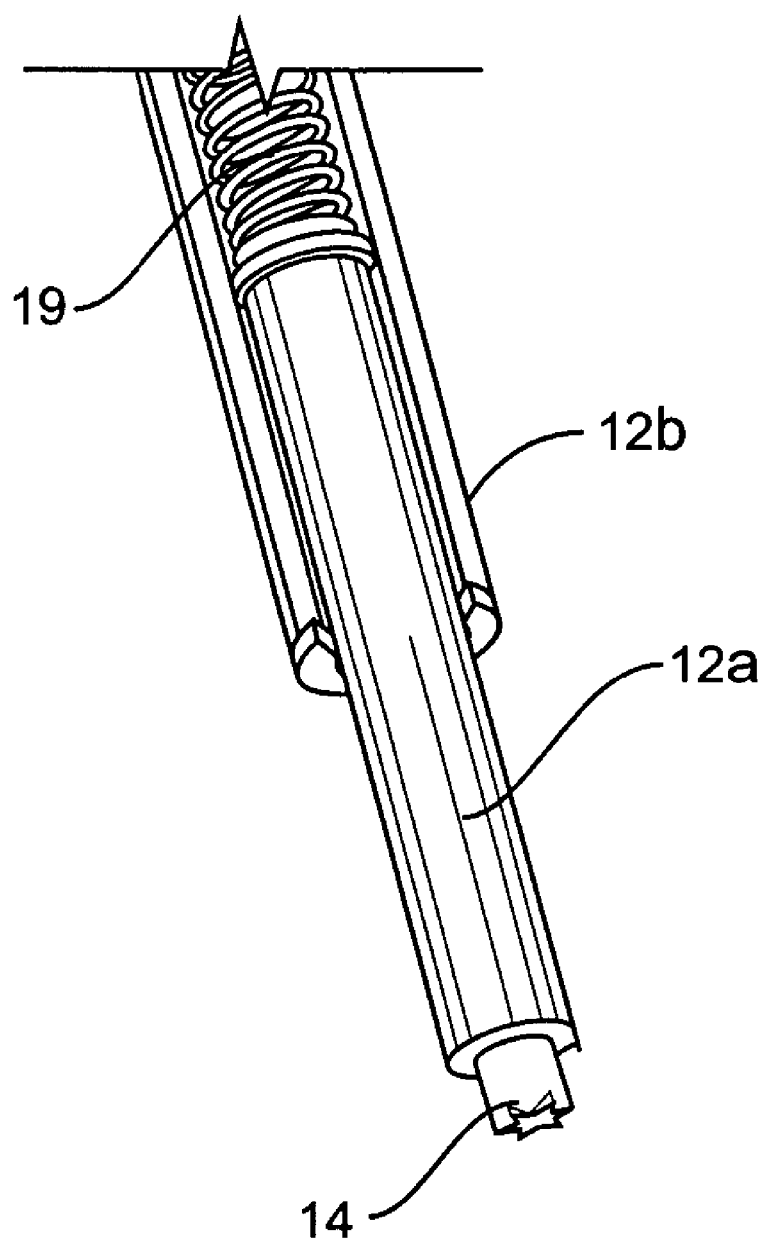
FIG. 7 is a partial schematic view of a spring-loaded shaft on the first element according to one embodiment of the present invention.

The shaft 12 may be spring-loaded having telescoping first and second shaft members and a biasing spring there between. FIG. 7 illustrates one embodiment of the spring loaded shaft 12 having a first section 12a that telescopes within a second section 12b. A spring 19 biases the first section 12a outward from the end of the second section 12b.

This configuration may be necessary when the shaft 12 is longer than the second element 20 to prevent the driver 14 from contacting the member 80 or bone prior to the striking surface 16 contacting the contact surface 27. Contact of the driver 14 may cause the striking and contact surfaces 16, 27 to remain spaced apart, and the force of the moving first element 20 to be directed to the driver 14. This could result in damage to the driver 14, member 80, bone, or a combination of all three.

The term "member" is used herein in a general sense to describe the element to which the device is mounted. In one embodiment, the member 80 is an implant that is left in the body. Examples of implants include a plate mounted on the exterior surface of a bone, a device mounted within the interior of a bone, and an intervertebral device mounted within the space formed between two adjacent vertebrae. In another embodiment, the member 80 is a jig which is a fixture or device to guide or hold a cutting, measuring, or space maintaining device in order to prepare a location, such as a vertebral body or disc space, in order to receive an implant. Jigs may also be used in a process to relieve symptoms of a spinal or neurological disorder.

Other embodiments of the present invention may be carried out in other specific ways than those herein set forth without departing from the scope and essential characteristics of the invention. In another embodiment, the force of the extensions 44 against the inner edges of the apertures 82 is adequate for maintaining the second element 20 attached to the member 80, therefore, no slots 84 are necessary in the member. The shaft 12 and handle 18 may be fixedly attached and rotation of the handle 18 causes rotation of the shaft 12. In one embodiment, a separate instrument, such as a hammer, is used to apply a striking force to the contact surface 27. In one embodiment, the coupler 24 includes threads that mate with threads within the aperture to attach the second element 20 to the member 80. The present embodiments are, therefore, to be considered in all respects as illustrative and not restrictive, and all changes coming within the meaning and equivalency range of the appended claims are intended to be embraced therein.

What is claimed is:

1. A surgical device for inserting a member within a patient, the device comprising:
   a first element having an elongated shaft with a driver at a first end and a substantially flat striking surface at a second end;
   a second element having a handle and a neck with a bore extending through a length of the second element, the handle having a contact surface that is substantially flat and parallel with the striking surface when the shaft is inserted within the bore, the neck having an extension that is positionable between an extended orientation that extends outward and has a first width greater than a width of the neck, and a retracted orientation with a second width less than or equal to the width of the neck, the neck further comprising a window opening into the bore and being spaced from the extension.

2. The device of claim 1, further comprising a second extension extending outward from the neck, the second extension being in proximity to the extension and being spaced from the window.

3. The device of claim 1, further comprising a flange having a flange width greater than the first width, the flange positioned between the extension and the window.

4. A surgical device to attach a member within a patient, the device comprising:
   a first element having a shaft extending outward from a first handle, the first handle having a striking surface that is substantially perpendicular to the shaft, the first element further comprising a driver on a distal end opposite from the first handle;
   a second element having a handle and a coupler with a bore extending a length of the second element, the coupler having an extension selectively positionable between an outwardly-extending first orientation having a first width and a retracted second orientation having a second width less than the first width, the handle having a contact surface that is contacted by the striking surface when the shaft is inserted within the bore, the contact surface and the striking surface being substantially parallel when the shaft is inserted within the bore, the second element further comprising a window positioned between the handle and the coupler and being operatively connected with the bore.

5. The device of claim 4, wherein the bore has a flared end within the handle.

6. The device of claim 4, wherein the shaft has a length greater than the second element.

7. The device of claim 4, further comprising a flange extending outward from the second element adjacent to the coupler, the flange being wider than the outwardly-extending first orientation of the extension.

8. The device of claim 4, wherein the coupler further comprises a second extension in proximity to the first extension and extending outward from the second element.

9. The device of claim 8, wherein one of the first and second extensions comprises an O-ring.

10. The device of claim 8, wherein one of the first and second extensions comprises a C-clip.

11. The device of claim 4, wherein the window is positioned closer to the handle than to the coupler.

* * * * *